United States Patent
Tam

[19]

[11] Patent Number: 5,881,123
[45] Date of Patent: Mar. 9, 1999

[54] SIMPLIFIED CONE BEAM IMAGE RECONSTRUCTION USING 3D BACKPROJECTION

[75] Inventor: Kwok Tam, Edison, N.J.

[73] Assignee: Siemens Corporate Research, Inc., Princeton, N.J.

[21] Appl. No.: 106,537

[22] Filed: Jun. 29, 1998

Related U.S. Application Data

[63] Continuation-in-part of Ser. No. 52,281, Mar. 31, 1998.

[51] Int. Cl.⁶ .................................................. A61B 6/03
[52] U.S. Cl. ........................................... 378/4; 378/901
[58] Field of Search .................................. 378/4, 15, 901

[56] References Cited

U.S. PATENT DOCUMENTS

| | | | |
|---|---|---|---|
| 5,257,183 | 10/1993 | Tam | 378/4 |
| 5,270,926 | 12/1993 | Tam | 378/4 |
| 5,390,226 | 2/1995 | Tam | 378/19 |
| 5,461,650 | 10/1995 | Tam | 378/4 |
| 5,463,666 | 10/1995 | Eberhard et al. | 378/4 |
| 5,491,735 | 2/1996 | Hsieh | 378/15 |
| 5,504,792 | 4/1996 | Tam | 378/15 |
| 5,805,659 | 9/1998 | Tam | 378/15 |

OTHER PUBLICATIONS

"Practical Cone–Beam Algorithm", Journal of the Optical Society of America A, vol. 1, Jun. 1984, pp. 612–614.

"Derivation and Implementation of a Cone–Beam Reconstruction Algorithm for Nonplanar Orbits", IEEE Transactions on Medical Imaging, vol. 13, No. 1, Mar. 1994, pp. 196–211.

"The Mathematics of Computerized Tomography", F. Natterer, Copyright 1986, John Wiley & Sons Ltd., pp. 102–110.

*Primary Examiner*—David P. Porta
*Assistant Examiner*—David Vernon Bruce
*Attorney, Agent, or Firm*—Lawrence C. Edelman

[57] ABSTRACT

A scanning and data acquisition method and apparatus for three dimensional (3D) computerized tomography (CT) imaging of a region-of-interest (ROI) in an object, wherein image reconstruction processing is applied to a plurality of sets of cone beam projection data, each set being acquired on a detector at a corresponding plurality of scan path source positions. A first image reconstruction processing step comprises applying a mask to each set of the projection data to form masked data sets. The mask for each data set is formed by cone beam projections onto the plane of the detector of portions of the source scan path that are above and below the source position that acquired the data set being masked. The next image reconstruction processing step comprises ramp filtering of each masked data set along a plurality of parallel lines formed therein that are parallel with and in the direction of a parallel projection into the data set of a line that is tangent to the scan path at the source position that acquired that data set and in the direction of the next source position, to generate filtered data sets. Each filtered data set is then subjected to a weighted 3D backprojection into a 3D space, thereby reconstructing in a piecewise manner a 3D image of the ROI in the object.

25 Claims, 5 Drawing Sheets

SIMPLIFIED CONE BEAM IMAGE RECONSTRUCTION USING 3D BACKPROJECTION

CROSS-REFERENCE TO RELATED APPLICATIONS

This is a continuation-in-part of application Ser. No. 09/052,281, filed Mar. 31, 1998.

BACKGROUND OF THE INVENTION

1. Field of the Invention

The invention relates generally to image reconstruction in a cone beam imaging system having a radiation source scan path that encircles an object, and more specifically to the use of a simplified 3D backprojection image reconstruction technique in a cone beam imaging system.

2. Description of the Prior Art

A filtered backprojection (FBP) cone beam image reconstruction technique is described by Kudo, H. and Saito, T., in their article entitled "Derivation and Implementation of a Cone-Beam Reconstruction Algorithm for Nonplanar Orbits", IEEE Trans. Med. Imag., MI-13 (1994) 196–211, incorporated herein by reference.

Briefly, the FBP technique consists of the following steps at each cone beam view (i.e., at each position of the radiation source as it scans about the object, and at which an imaging detector acquires a corresponding set of projection data):

1. Compute a 1D projection (i.e., line integral) of the measured cone beam image acquired on a detector plane 1 at each of a plurality of angles θ. This step is illustrated by FIG. 1A for a given angle $\theta_1$ of a plurality of angles θ, where the projection 2 at coordinates (r,θ) comprises the integrated values of the cone beam image 4 on detector plane 1 along plurality of parallel lines L(r,θ) that are normal to angle θ, each line L being at an incremental distance r from an origin O. Generally, if the detector plane 1 comprises an N by N array of pixels, then the number of angles θ is typically given by πN/2.

2. Filter each 1D projection in accordance with a d/dr filter, resulting in a new set of values at each of the r,θ coordinates, such as shown by filtered projection 6 for the angle $\theta_1$ in FIG. 1A.

3. Normalize the filtered projections with a normalization function M(r,θ). Normalization is needed to take into account the number of times the plane of integration Q(r,θ) which intersects the source position and the line L(r,θ), intersects the scan path, since the data developed at each scan path intersection creates a contribution to the image reconstruction on the plane Q(r,θ).

4. Backproject the filtered projection 6 from each angle θ into a 2D object space 7 which coincides with the detector plane 1. This step is illustrated by FIG. 1B, wherein lines 8 spread the value from each r,θ coordinate into 2D space 7 in a direction normal to each θ.

5. Perform a 1D d/dt filtering of the backprojection image formed in 2D space 7 by step 4. The 1D filtering is performed in the direction of the scan path, i.e., along lines 10, where t points in the direction of the scan path.

6. Perform a weighted 3D backprojection of the resulting data in 2D space 7 (i.e., from each pixel in the detector) onto a plurality of sample points P in a 3D object volume 12. The density assigned to each point P is weighted by the inverse of the square of the distance between the point and the apparent x-ray source (see Equation (59) of the forenoted Kudo et al article).

The above prior art procedure will be referred to hereinafter as the 6-step process. It is assumed in this process that the entire cone beam image of the object is captured on the detector of the imaging system. Consider a plane Q(r,θ), which intersects the object, formed by the source and the line L(r,θ) on the detector at angle θ and at a distance r from the origin. Ignoring the function M(r, θ), the operations 1 through 6 compute the contribution to the reconstructed object density on the plane Q(r,θ) from the x-ray data illuminating the plane and its immediate vicinity. Since the 6-step process is detector driven, a contribution from the data illuminating the plane is computed every time the plane intersects the scan path and thus is illuminated by the x-ray beam. Consequently, the function M(r,θ) is used after the filter function in step 2 to normalize the results. Normalization is particularly undesirable since it requires pre-computing and storing a 2D array M(r,θ) for each source position along an imaging scan path. Since there are usually hundreds, if not thousands of source positions, this type of normalization is both computationally intensive and resource (computer memory) expensive. In the Kudo et al article, however, at page 203 it is noted that in the special case where the scan path is a circle, steps 1–5 can be simplified into a single convolution step, which essentially comprises ramp filtering the cone beam image in the direction of the scan path. This ramp filtering is equivalent to the well-known Feldkamp algorithm for a single circular orbit, such algorithm being described in particular detail in the article by L. A. Feldkamp, L. C. Davis, and J. W. Kress, entitled "Practical cone-beam algorithm" published in the J. Opt. Soc. Am. A. Vol. 1, 1984, pages 612–619 (see in particular the convolution function equations 15 and 16 at page 614, which describe the convolution function as:

$$g(Y) = Re \int_0^{\omega y0} \exp(i\omega Y)\omega d\omega,$$

incorporated by reference herein. The key to this simplification is that in the case of a circular scan path, the normalization function M(r,θ) is a constant, equal to 2. Consequently, the filtered projection at each r,θ that results after step 2, can merely be divided by 2 to compensate for the data redundancy.

It would be desirable to use this simplification for source scan paths other than a single circle, but the Kudo et al article does not provide any indication how this can be done, or that it is even possible.

Furthermore, since the above procedure assumes that the detector captures the entire cone beam image of the object at each view, it can not be applied to a cone beam imager having a short detector, i.e., one that only captures a portion of the cone beam image at each cone beam view. Thus, in its current form, the Kudo et al. FBP technique cannot be applied to a cone beam imager having a spiral scan path and employing a short detector.

It would be desirable to apply the Kudo et. al. image reconstruction processing simplification for a single circle scan imager, to a cone beam imaging system that not only has a spiral scan path, but also uses a short detector.

SUMMARY OF THE INVENTION

A scanning and data acquisition method and apparatus for three dimensional (3D) computerized tomography (CT) imaging of a region-of-interest (ROI) in an object, wherein image reconstruction processing is applied to a plurality of sets of cone beam projection data, each set being acquired on a detector at a corresponding plurality of scan path source positions. A first image reconstruction processing step comprises applying a mask to each set of the projection data to form a masked data set, wherein data in the set that is outside the mask is set to zero. The mask for each data set is formed by cone beam projections onto the plane of the detector of portions of the source scan path that are above and below the source position that acquired the data set being masked. The next image reconstruction processing step comprises ramp filtering of each masked data set along a plurality of parallel lines formed therein that are parallel with and in the direction of a parallel projection into that data set of a line that is tangent to the scan path at the source position that acquired that data set and in the direction of the next source position, to generate a filtered data set. Each filtered data set is then subjected to a weighted 3D backprojection into a 3D space, thereby reconstructing in a piecewise manner a 3D image of the ROI in the object.

DETAILED DESCRIPTION OF THE INVENTION

Figure 1A:
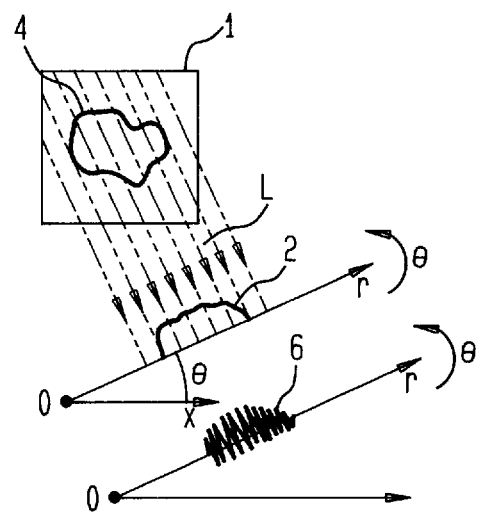
FIGS. 1A and 1B illustrate the Kudo et. al. prior art 3D backprojection approach for cone beam image reconstruction, previously described.
Figure 1B:
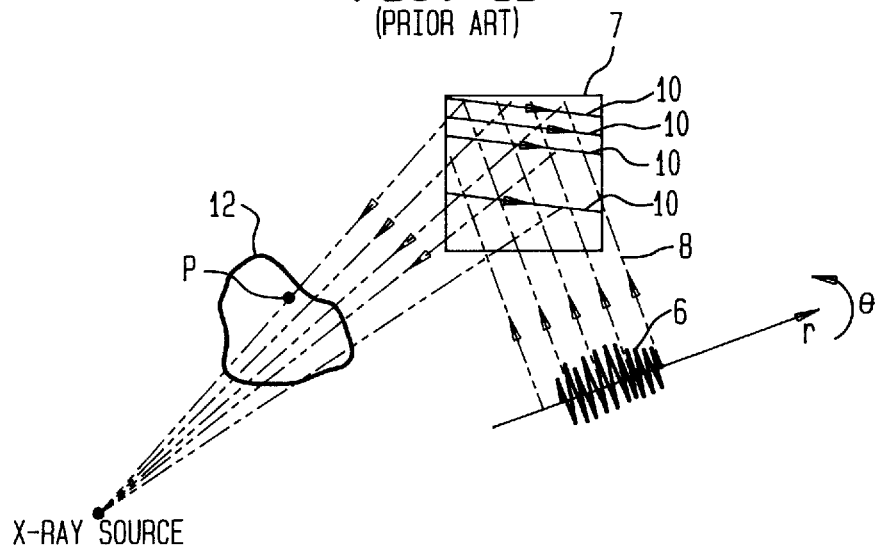
Figure 2:
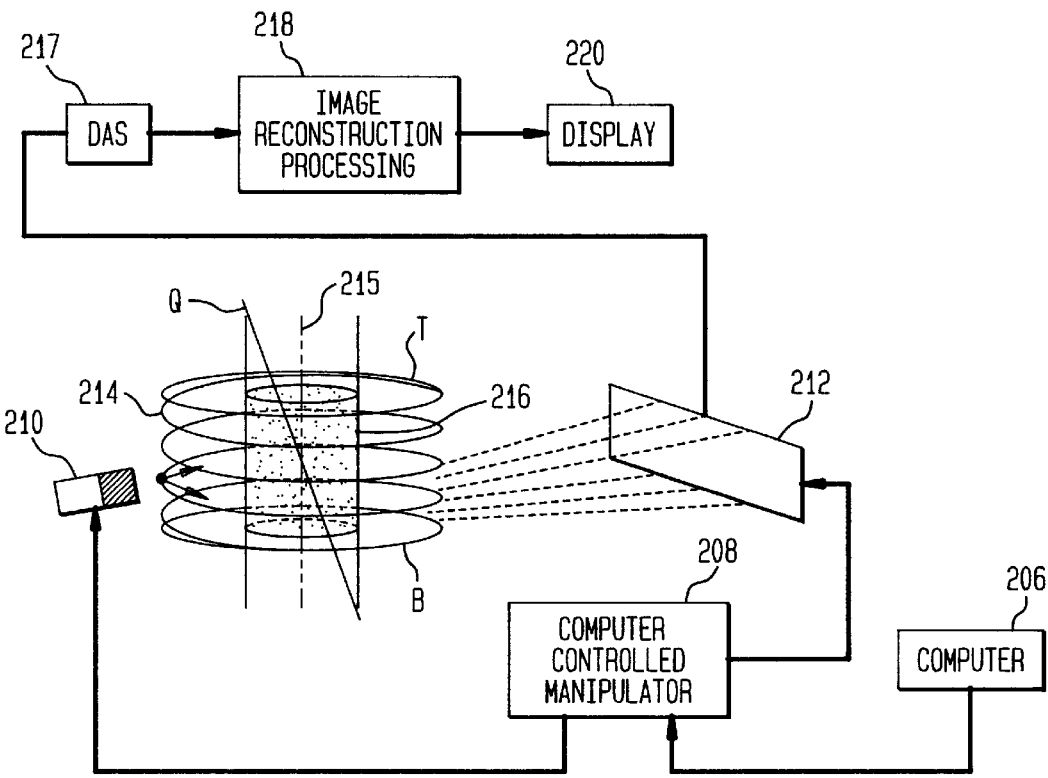
FIG. 2 illustrates a cone beam imaging apparatus useful for performing image reconstruction in accordance with the principles of the invention.

FIG. 2 illustrates a cone beam 3D CT imaging apparatus useful for acquiring and processing acquired projection data in accordance with the principles of the present invention. The illustrated imaging apparatus is constructed and operates substantially in accordance with same principles described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993 and U.S. Pat. No. 5,453,666 entitled HELICAL AND CIRCLE SCAN REGION OF INTEREST COMPUTERIZED TOMOGRAPHY issued Oct. 31, 1995, incorporated herein by reference, except as to be specifically described later with respect to implementation of image reconstruction processing in accordance with the present invention.

As shown in FIG. 2, in response to control signals from an appropriately programmed computer 206, a computer controlled manipulator 208 causes a source 210 of a cone or pyramid shaped beam of energy (such as x-rays) and a two-dimensional pixelated detector array 212 to cooperate (scan) at a plurality of discreet, sequentially occurring adjacent source positions, along a pre-defined source scanning path. In the illustrated embodiment the scanning path is shown as a spiral scan path 214 centered on a predetermined axis 215 of an object 216. Other types of scan paths that encircle and traverse object 216 can also be used, however, as will become apparent later, a scan path 214 exhibiting a high degree of symmetry in its parallel projection is preferred.

The only height requirement on the detector is that it's height should be more than the distance between adjacent turns of a projection of the spiral scan path on the detector. If only an ROI of object 316 is to be imaged, in a preferred embodiment, the known technique of providing a top circle scan T at the top level of the ROI and a bottom circle scan B at the bottom level of the ROI, are added.

As a result of the source/detector cooperation under control of computer 206 and manipulator 208, at each of the source positions along path 214, x-ray energy passes through the field of view of the imaging apparatus, is attenuated by object 216, and a set of projection data corresponding to the sensed x-ray energy falling on the elements (pixels) within detector 212 is developed. Each set of projection data is supplied to a data acquisition system (DAS) 217 which, like the previously described portions of FIG. 2, may operate in a fashion well known to those of ordinary skill in this technology for digitizing and storing of the acquired projection data.

In my above-noted U.S. Pat. Nos. 5,257,183 and 5,453,666, image reconstruction processing 218 is provided by Radon space driven conversions, thereby developing an image reconstruction of object 216 on a display 220. It would be desirable to find a way to use the fitered backprojection technique noted in the forenoted Kudo et al. article, and in particular the simplification principles applicable for a single circular scan, in conjunction with the image reconstruction processor 218 of FIG. 2.

The present inventor has devised a way to incorporate the technique of data combination for ROI reconstruction, with the the Kudo et. al. image reconstruction processing simplification for a single circle scan imager, thereby providing a cone beam imaging system that not only can have a spiral scan path, but can also use a short detector.

Consequently, the image reconstruction processing is greatly speeded-up due to a reduced need for extensive computations, the requirement of significant memory allocation for normalization step 3 of the 6-step process is obviated, and furthermore, the imaging system can use a detector that does not acquire at each source position a complete view of the ROI of the object.

Accordingly, in accordance with one aspect of the present invention, instead of division by the function $M(r,\theta)$ as done in the Kudo et al. 6-step process, normalization of the reconstructed object densities is achieved by dividing the x-ray beam coverage of plane $Q(r,\theta)$ between the various source positions that illuminate the plane without any overlap.

Figure 3:
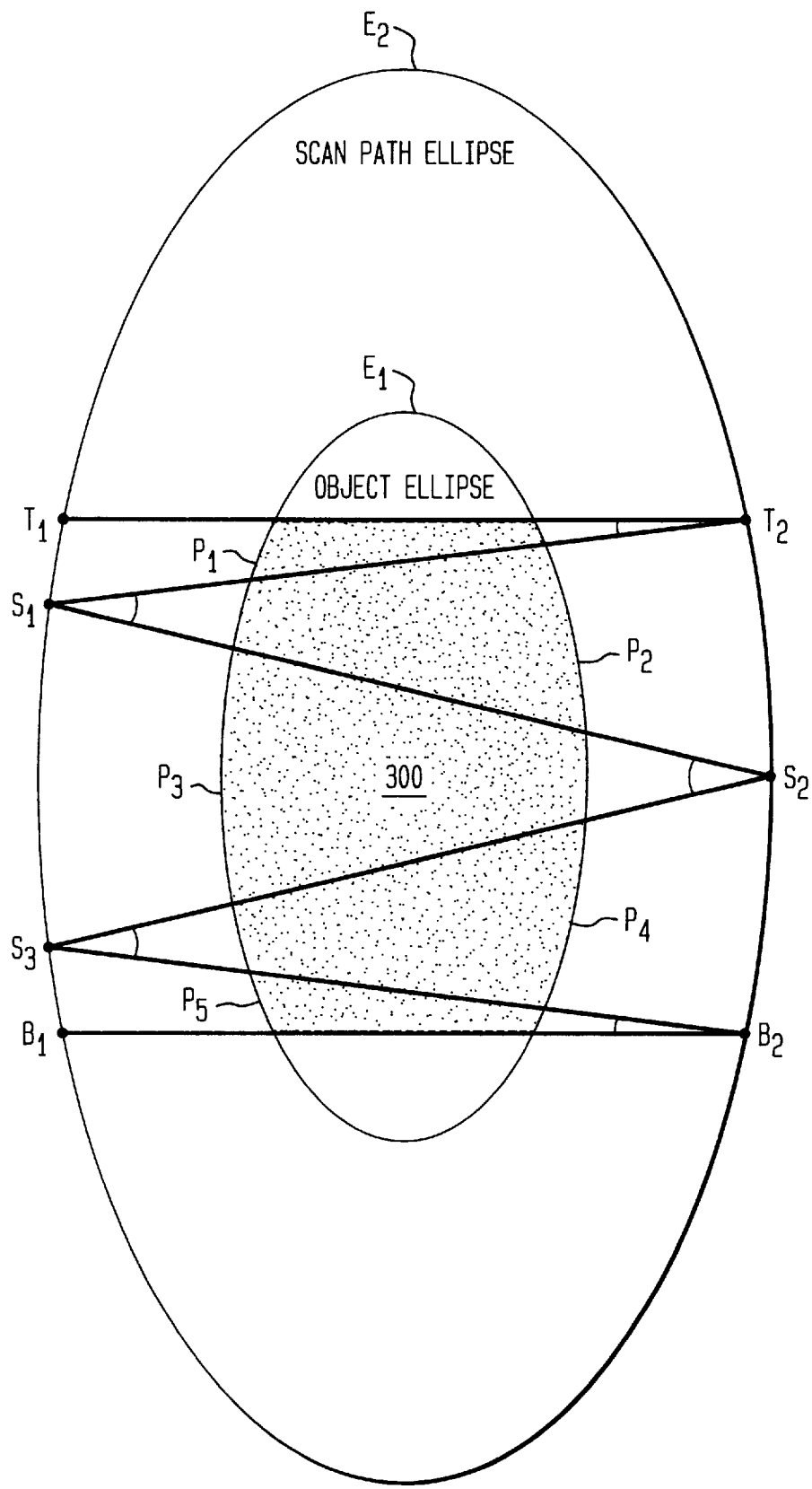
FIG. 3 illustrates a procedure for data combination in accordance with one aspect of the present invention.

More specifically, this concept of the division of x-ray beam coverage is illustrated in FIG. 3, which represents a typical integration plane $Q(r,\theta)$ intersecting cylindrical object 216 and the spiral scan path 214, which is assumed to wrap around object 216 on an imaginary cylinder. An edge view of plane Q is illustrated in FIG. 2. Since a non-vertical plane will intersect a cylinder in an ellipse, the plane $Q(r,\theta)$ intersects object 216 and the cylindrical spiral scan path 214 in 2 ellipses, one inside the other.

The intersection of the integration plane Q with the object cylinder is indicated by the smaller ellipse $E_1$, and its intersection with the scan path cylinder is indicated by the larger ellipse $E_2$. Since spiral path 214 lies on the scan path cylinder, it intersects the plane Q in points that lie on the ellipse $E_2$. These source positions are shown as $S_1$, $S_2$, and $S_3$ in the FIG. 3. Similarly, it is easy to see that the top scan path circle intersects the plane in two points $T_1$ and $T_2$ which lie at the intersection between $E_2$ and the top edge of the object's region-of-interest (shaded portion of object 216), and that the bottom circle intersects the plane in the two points $B_1$ and $B_2$ which lie at the intersection between $E_2$ and the bottom edge of the object's region-of-interest. Other integration planes may have more or less spiral scan path intersections, depending upon their orientation, and may not intersect either of the top or the bottom circle scan paths.

As is apparent from FIG. 3, the source positions which illuminate that portion of integration plane Q that lies within the region-of-interest (shaded area 300), are $T_2$, $S_1$, $S_2$, $S_3$, and $B_2$. Complete X-ray coverage of region-of-interest 300 of this portion of the integration plane can be achieved by suitably combining the data acquired at these 5 source positions, as indicated in FIG. 3. For example, at $T_2$ we only use the cone beam data within the angle bound by $T_1T_2$ and $S_1T_2$, and at $S_1$ we only use the cone beam data within the angle bound by $T_2S_1$ and $S_2S_1$. And so on. Five partial planes P1 through P5 are therefore defined by the source positions $T_2$, $S_1$, $S_2$, $S_3$, and $B_2$, which do not overlap and together completely cover the portion of plane Q that lies within the region-of-interest of object 216, i.e., ROI300. In this way the totality of the cone beam data from each of the contributing source positions illuminates the entire plane $Q(r,\theta)$ only once without any overlap. Further details of this data combination technique can be found in my earlier cone beam patents, such as U.S. Pat. No. 5,463,666.

Because only specific non-overlapping contributions to the Radon data are developed from the projection data, the function $M(r,\theta)$ can be set to unity for all cone beam views. Thus, as the detector data acquired at each of the source positions is processed, as next described, contributions to each plane intersecting the ROI are reconstructed only once.

In accordance with the principles of the present invention, two modifications are made to the simplified 6-step process to enable its use in a cone beam imaging system that not only has a spiral scan path, but also uses a short detector.

Modification 1

Figure 4:
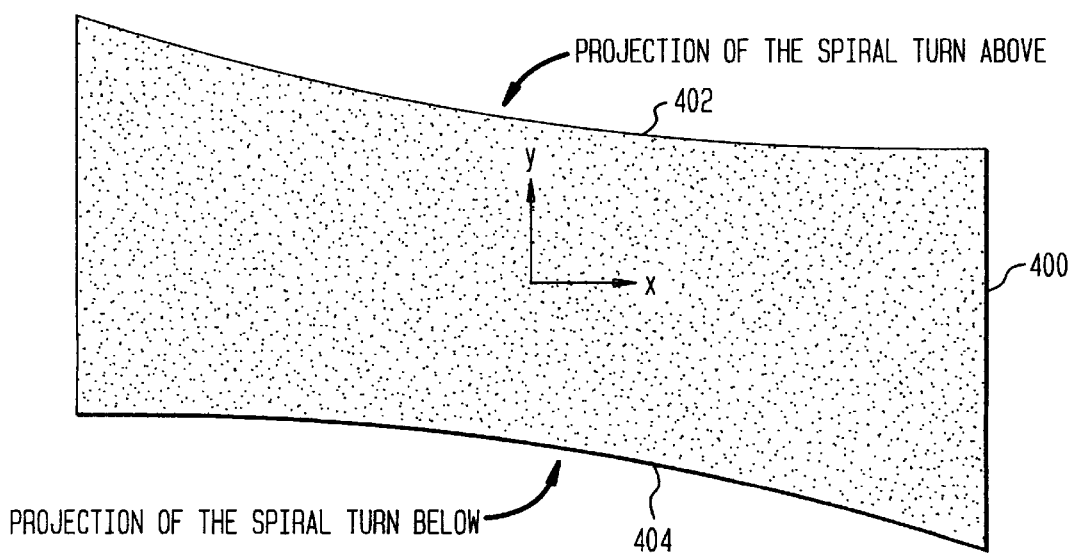
FIGS. 4, 6 and 7 illustrate masks useful for processing acquired cone beam projection data in accordance with the principles of the invention.

As previously described above in conjunction with FIG. 3, the acquired cone beam projection data should be restricted to the appropriate angular range, to avoid data redundancy, and thereby avoid the need for normalization function $M(r,\theta)$. This can be accomplished using a masking process. In general, the masking of acquired cone beam projection data is well known, for example see my earlier U.S. Pat. No. 5,504,792 issued Apr. 2, 1996. FIG. 4 illustrates a mask 400 constructed in accordance with this aspect of the present invention. Mask 400 consists of a top curve 402 and a bottom curve 404, each curve being formed by cone beam projections of the spiral scan path turn above and the spiral scan path turn below the current source position, onto the detector (212 of FIG. 2). For a flat detector located at the rotation axis such that a line connecting the source to the detector origin is normal to the detector plane, the equation for top curve 402 for the spiral scan path projection is given by:

$$y = \frac{h}{2\pi} \tan^{-1}\left(\frac{a}{x}\right)\left(1 + \frac{x^2}{a^2}\right) \quad \text{for } x \geq 0 \quad (1)$$

$$y = \frac{h}{2\pi} \left[\pi + \tan^{-1}\left(\frac{a}{x}\right)\right]\left(1 + \frac{x^2}{a^2}\right) \quad \text{for } x < 0$$

where x and y are the Cartesian coordinate axes of the detector, with the y axis coinciding with the rotation axis, a is the radius of the spiral, and h is the distance between adjacent spiral turns (the pitch). Bottom curve 404 is a reflection of top curve 402 about the origin, i.e. $(x,y) \rightarrow (-x,-y)$.

Figure 5:
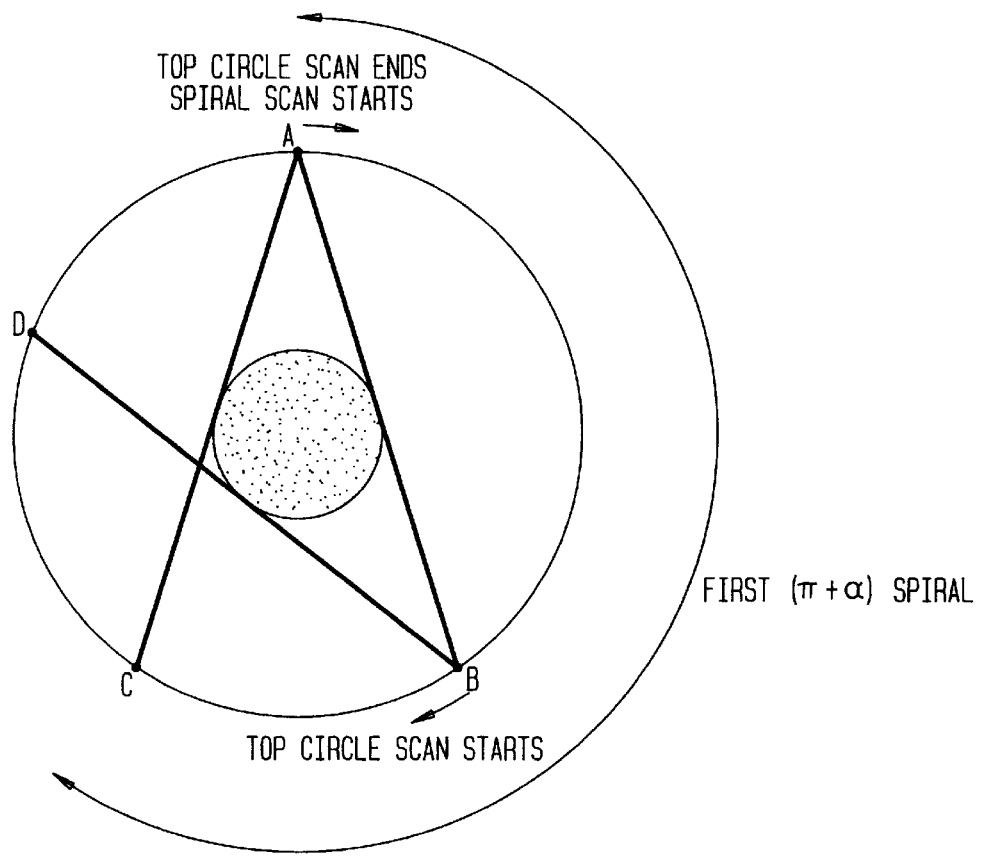
FIG. 5 is useful for understanding the generation of the masks shown in FIGS. 4, 6 and 7.
Figure 6:
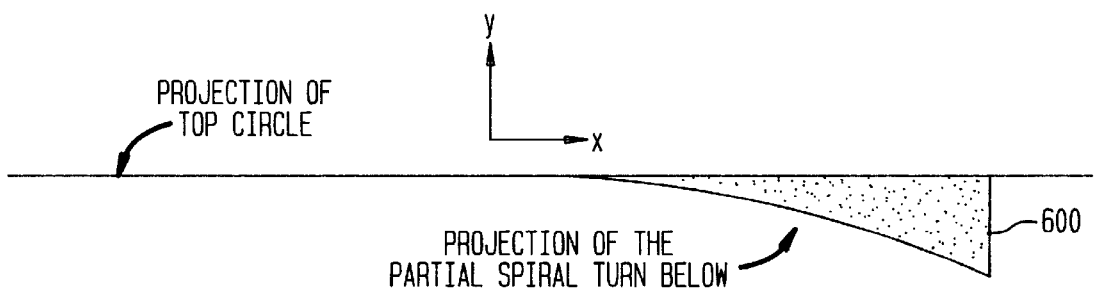
Figure 7:
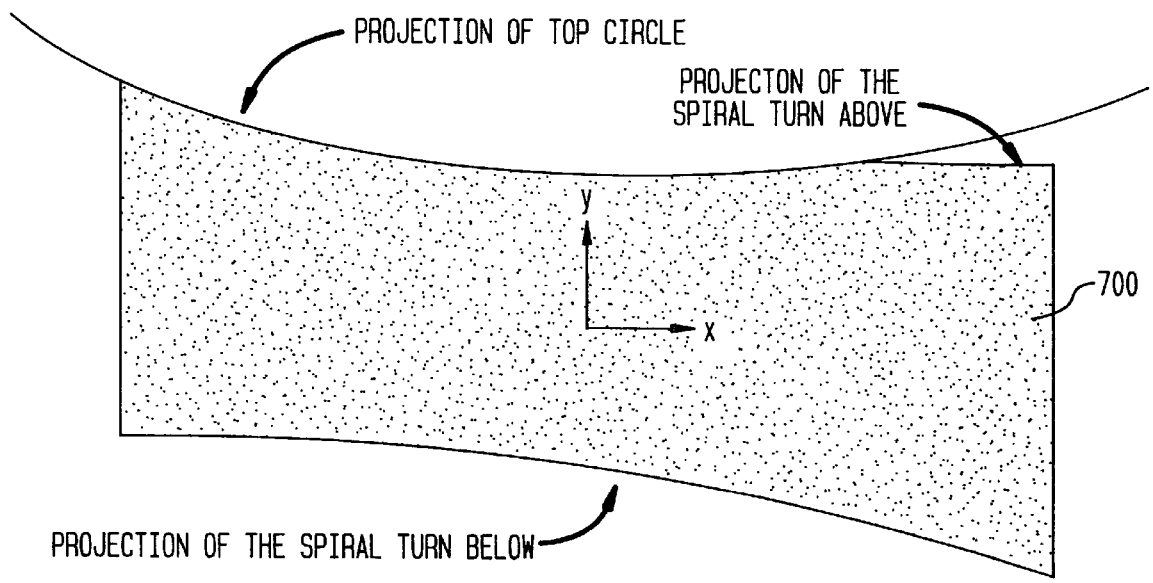

As described in conjunction with FIG. 2, for ROI imaging, circular arc scans are needed at the top and bottom levels. The top circle scan T starts at the angle $(\pi+\alpha)$ before the start of the spiral scan, and the bottom circle scan B ends at the angle $(\pi+\alpha)$ after the end of the spiral scan, where $\alpha$ is the fan angle of the x-ray beam. The detailed geometry of the precise mask used at each source position depends on the location of the source in the scan path. Accordingly, one can divide the spiral scan path into 5 distinct regions, as illustrated in FIG. 5. The first region comprises the last $(\pi+\alpha)$ turn of the top circle (clockwise from B to A). The second region comprises the first $(\pi+\alpha)$ turn of the spiral (clockwise from A to C). The third region comprises the interior portion of the spiral, i.e. after the first $(\pi+\alpha)$ turn and before the last $(\pi+\alpha)$ turn. The fourth region comprises the last $(\pi+\alpha)$ turn of the spiral (similar to the second region). The fifth region comprises the first $(\pi+\alpha)$ turn of the bottom circle (similar to the first region, but at the bottom). The masks for these 5 regions are described in greater detailed below, and are illustrated in FIGS. 6–7. These Figures assume the radiation source rotates in a spiral path from top to bottom in a clockwise direction.

(1) For the last $(\pi+\alpha)$ turn of the top circle, see mask 600 of FIG. 6, wherein:
Top curve: a horizontal line at the level of the top circular arc; and
Bottom curve: a reflection of Equation (1) about the origin.

(2) For the first $(\pi+\alpha)$ turn of the spiral, see mask 700 of FIG. 7, wherein:
Top curve: the intersection of two curves: the standard top spiral mask, Equation (1), and the cone beam projection of the top circle projected from the source given by the equation:

$$y = b\left(1 + \frac{x^2}{a^2}\right)$$

where 2b is the distance between the top and bottom circles.
Bottom curve: reflection of Equation (1) about the origin (3) For the interior portion of the spiral, see mask 400 of FIG. 4, wherein:
Top curve: Equation (1)
Bottom curve: reflection of Equation (1) about the origin (4) For the last $(\pi+\alpha)$ turn of the spiral, see mask 700 of FIG. 7, but rotated by 180°

(5) For the first $(\pi+\alpha)$ turn of the bottom circle, see mask 600 of FIG. 6, but rotated by 180°

Thus, in accordance with one aspect of the invention, a first step required to incorporate the principles of the simplified 6-step process into a cone beam imaging apparatus having a short detector, comprises bounding the set of projection data acquired by the detector at each source postion, with an appropriate one of the masks of FIGS. 4 and 6–7. In accordance with the general principles of masking, data in the set that is outside the mask is changed to a zero value, while data that is inside the mask is left unchanged. After a set of projection data is bound by an appropriate mask, it is referred to herein as a masked set of projection data, or more simply as a masked data set. Since the masks are formed by cone beam projection of the spiral turn above and the turn below the current source position, the masked segment corresponds exactly to the angular range bound by the prior and the subsequent source positions as required by the data combination principles illustrated in FIG. 3. Computer 206 of FIG. 2 can compute masks 400 "on-the-fly" during image reconstruction, or they could be pre-calculated and stored in system memory.

Modification 2

Figure 8:
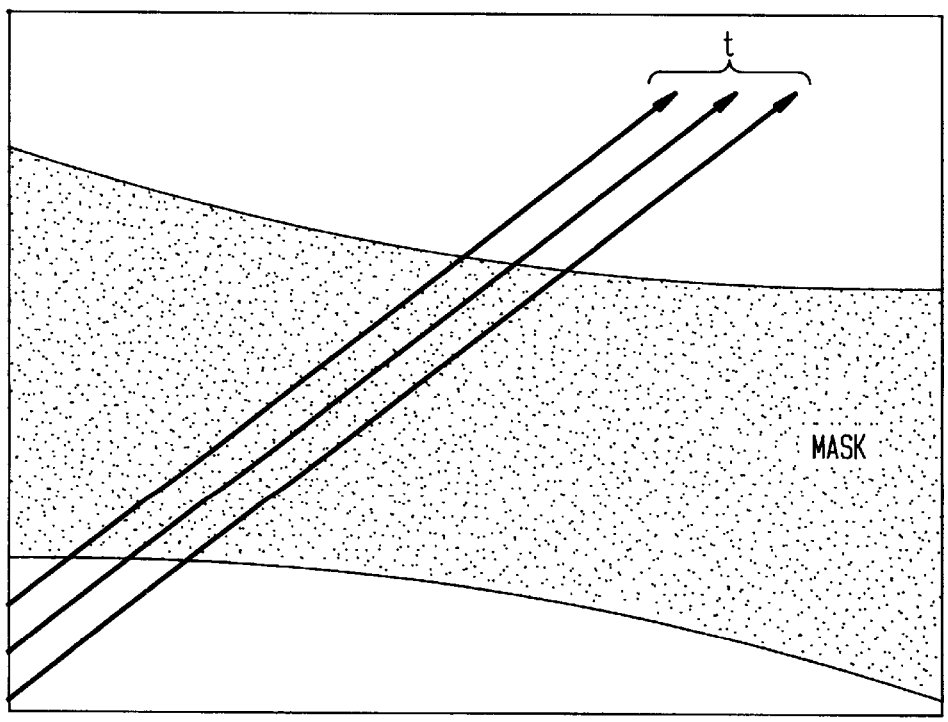
FIG. 8 illustrates use of a mask for processing acquired cone beam projection data in accordance with the principles of the invention.

In accordance with a second aspect of the invention, the Feldkamp ramp filtering technique is applied to the masked sets of projection data, thereby simplifing steps 1 through 5 of the prior art 6-step process into a single ramp filtering step, as illustrated in FIG. 8. More specfically, each set of masked data is ramp filtered along a plurality of parallel lines t formed therein that are parallel with and in the direction of a parallel projection into the data set of a line that is tangent to the scan path at the source position that acquired that data set and in the direction of the next source position. Ramp filtering of each masked data set along these lines generates a corresponding plurality of filtered data sets, where the data at each point along each line represents a summation of the Radon data at that point, as would have been developed by steps 1 through 5 of the Kudo et al 6-step process.

Although the single step of ramp filtering is much faster than using the prior art steps 1–5, there is a tradeoff, or price to pay, i.e., the developed Radon data is somewhat less accurate than needed to provide an exact reconstruction. This is due the fact that when calculating the line integral derivative data in the Kudo et al 6-step process, there is no masking of the projection data. Likewise, in the modification of the Kudo el al process as described in the inventor's forenoted parent application U.S. Ser. No. 09/052,281, there is no masking of the projection data, only of the extent of the lines L for which line integral derivatives are calculated. That is, for example, as described in U.S. Ser. No. 09/052, 281, line integrals for the adjacent lines L1 and L2 are not masked, and in fact, detector rows above and below the detector rows defining the lines L are used to determine these line integrals. Masking only takes place on the lines L, after the line integrals for lines L1 and L2 have been subtracted to calculate the line integral derivatives for the lines L. However, as a necessary consequence of ramp filtering of the masked projection data in accordance with the present invention, it is implied that the extent of the lines L1 and L2 are also limited by their intersection with the mask. Although this theoretically leads to a somewhat less than exact reconstruction, in view of the tradeoff of improved image reconstruction speed, the present invention has useful applications.

Thus, there has been shown and described a novel method and apparatus for allowing the use of a simplified 3D backprojection image reconstruction technique in a cone beam CT imaging apparatus having a relatively small detector. Many changes, modifications, variations and other uses and applications of the subject invention will, however, become apparent to those skilled in the art after considering this specification and its accompanying drawings, which disclose preferred embodiments thereof. For example, the ramp filtering can be accomplished by processing the masked data sets in Fourier space, as compared with the illustrated real space filtering. Additionally, as previously noted, other scan paths can be used. All such changes, modifications, variations and other uses and applications which do not depart from the teachings herein are deemed to be covered by this patent, which is limited only by the claims which follow as interpreted in light of the foregoing description.

I claim:

1. A scanning and data acquisition method for three dimensional (3D) computerized tomography (CT) imaging of a region-of-interest (ROI) in an object, comprising the steps of:

applying radiation energy from a cone beam source to at least the ROI of the object;

defining a source scanning trajectory as a scan path traversed by the source;

using the cone beam source, fixed relative to an area detector with both source and detector movably positioned relative to the object, to scan about the ROI in the object along the scan path;

scanning at a plurality of source positions in a direction along the scan path to cause said area detector to acquire a set of cone beam projection data at each of said source positions;

applying a mask to each set of the projection data to form masked data sets;

convolution processing each masked data set along a plurality of parallel lines formed therein that are parallel with and in the direction of a parallel projection into the data set of a line that is tangent to the scan path at the source position that acquired that data set and in the direction of scanning, to generate filtered data sets;

subjecting the data of each filtered data set to a weighted 3D backprojection into a 3D space, thereby reconstructing in a piecewise manner a 3D image of the ROI in the object.

2. The method of claim 1, wherein said applying step includes a forming step for forming the mask for each data set by cone beam projecting onto the plane of the detector portions of the source scan path that are above and below the source position that acquired the data set being masked.

3. The method of claim 2, wherein the forming step forms a mask for each source position that has a top curve and a bottom curve, and all of the projection data outside the top and bottom curves of the mask are set to zero, for forming the masked data sets.

4. The method of claim 3, wherein the source scanning trajectory is defined as a spiral scan path that surrounds the ROI in the object, and is connected to a first scan path circle at a top portion of the ROI in the object, and a second scan path circle at a bottom portion of the ROI in the object.

5. The method according to claim 4, wherein at source positions of the scan path at the top of the ROI in the object, the top curve of the mask includes a horizontal line portion formed from a projection of the first scan path circle, and the bottom curve of the mask is formed from a projection of the spiral scan path.

6. The method according to claim 4, wherein at source positions of the scan path at the bottom of the ROI in the object, the top curve of the mask is formed from a projection of the spiral scan path, and the bottom curve of the mask includes a horizontal line portion formed from a projection of the second scan path circle.

7. The method according to claim 5, wherein the top curve is formed from an intersection of a projection of the first scan path circle and a projection of the spiral scan path.

8. The method according to claim 6, wherein the bottom curve is formed from an intersection of a projection of the second scan path circle and a projection of the spiral scan path.

9. The method of claim 1, wherein the convolution processing step comprises a ramp filtering of the masked data set.

10. The method of claim 9, wherein the convolving processing comprises the function:

$$g(Y) = Re \int_0^{\omega y0} \exp(i\omega Y)\omega d\omega.$$

11. The method of claim 1, wherein the weighted 3D backprojection step comprises performing a weighted 3D backprojection of the data of each of the filtered data sets onto a plurality of sample points in a 3D object volume.

12. The method of claim 11, wherein the 3D object volume corresponds to the ROI volume in the object that is scanned by the cone beam source.

13. The method of claim 12, wherein the weight assigned to the filtered data that is backprojected to each sample point in the 3D object volume, is proportional to the inverse of the square of the distance between each sample point and the location of the cone beam source that acquired that data set being backprojected.

14. Apparatus for three dimensional (3D) computerized tomography (CT) imaging of a region-of-interest (ROI) in an object, comprising:
- a cone beam source for applying radiation energy to at least the ROI of the object;
- an area detector for detecting radiation energy;
- means for defining a source scanning trajectory as a scan path traversed by the source;
- a manipulator for causing the cone beam source, fixed relative to an area detector with both source and detector movably positioned relative to the object, to scan about the ROI in the object at a plurality of source positions in a direction along the scan path to cause said area detector to acquire a set of cone beam projection data at each of said source positions;
- a masking means for applying a mask to each set of the projection data to generate masked data sets;
- a convolution processing means for convolution processing each masked data set along a plurality of parallel lines formed therein that are parallel with and in the direction of a parallel projection into the data set of a line that is tangent to the scan path at the source position that acquired that data set and in the direction of scanning, to generate filtered data sets; and
- 3D backprojection means for subjecting the data of each filtered data set to a weighted 3D backprojection into a 3D space, thereby reconstructing in a piecewise manner a 3D image of the ROI in the object.

15. The apparatus of claim 14, wherein said masking means forms the mask for each data set by cone beam projecting onto the plane of the detector portions of the source scan path that are above and below the source position that acquired the data set being masked.

16. The apparatus of claim 14, wherein the masking means forms a mask for each source position that has a top curve and a bottom curve, and all of the projection data outside the top and bottom curves of the mask are set to zero, for forming the masked data sets.

17. The apparatus of claim 16, wherein the means defining the source scanning trajectory defines it as a spiral scan path that surrounds the ROI in the object, which path is connected to a first scan path circle at a top portion of the ROI in the object, and a second scan path circle at a bottom portion of the ROI in the object.

18. The apparatus of claim 17, wherein at source positions of the scan path at the top of the ROI in the object, the top curve of the mask includes a horizontal line portion formed from a projection of the first scan path circle, and the bottom curve of the mask is formed from a projection of the spiral scan path.

19. The apparatus of claim 17, wherein at source positions of the scan path at the bottom of the ROI in the object, the top curve of the mask is formed from a projection of the spiral scan path, and the bottom curve of the mask includes a horizontal line portion formed from a projection of the second scan path circle.

20. The apparatus of claim 18, wherein the top curve is formed from an intersection of a projection of the first scan path circle and a projection of the spiral scan path.

21. The apparatus of claim 19, wherein the bottom curve is formed from an intersection of a projection of the second scan path circle and a projection of the spiral scan path.

22. The apparatus of claim 14, wherein the convolution processing means performs a ramp filtering of the masked data set.

23. The apparatus of claim 14, wherein the weighted 3D backprojection means performs a weighted 3D backprojection of the data of each of the filtered data sets onto a plurality of sample points in a 3D object volume.

24. The apparatus of claim 23, wherein the 3D object volume corresponds to the ROI volume in the object that is scanned by the cone beam source.

25. The apparatus of claim 24, wherein the weight assigned to the filtered data that is backprojected to each sample point in the 3D object volume, is proportional to the inverse of the square of the distance between each sample point and the location of the cone beam source that acquired that data set being backprojected.

* * * * *